(12) United States Patent
Graf (10) Patent No.: US 9,517,125 B2
(45) Date of Patent: *Dec. 13, 2016

(54) ATTACHMENT DEVICE TO ATTACH TISSUE GRAFT (71) Applicant: Smith & Nephew, Inc., Memphis, TN (US)

(72) Inventor: Ben K Graf, Madison, WI (US)

(73) Assignee: Smith & Nephew, Inc., Memphis, TN (US)

( * ) Notice: Subject to any disclaimer, the term of this patent is extended or adjusted under 35 U.S.C. 154(b) by 252 days.

This patent is subject to a terminal disclaimer.

(21) Appl. No.: 14/224,603

(22) Filed: Mar. 25, 2014

(65) Prior Publication Data

US 2014/0296910 A1    Oct. 2, 2014

Related U.S. Application Data (62) Division of application No. 13/248,598, filed on Sep. 29, 2011, now Pat. No. 8,721,683.

(51) Int. Cl.
*A61B 17/04* (2006.01)
*A61F 2/08* (2006.01)

(52) U.S. Cl.
CPC ...... *A61F 2/0811* (2013.01); *A61F 2002/0817* (2013.01); *A61F 2002/0823* (2013.01); *A61F 2002/0829* (2013.01); *A61F 2002/0841* (2013.01); *A61F 2002/0847* (2013.01); *A61F 2002/0852* (2013.01); *A61F 2002/0864* (2013.01); *A61F 2002/0882* (2013.01)

(58) Field of Classification Search
CPC ............ A61F 2/0811; A61F 2002/0817; A61F 2002/0823; A61F 2002/0829; A61F 2002/0841;A61F 2002/0847; A61F 2002/0852; A61F 2002/0882

See application file for complete search history.

(56) References Cited

U.S. PATENT DOCUMENTS 5,306,301 A    4/1994    Graf et al.
5,769,894 A    6/1998    Ferragamo
(Continued)

FOREIGN PATENT DOCUMENTS

FR    2815843 A1    5/2002
GB    2370227 A     6/2002
(Continued)

OTHER PUBLICATIONS

First Office Action for related Chinese Application No. 201280058673 issued Jul. 1, 2015.
(Continued)

*Primary Examiner* — Robert Lynch
(74) *Attorney, Agent, or Firm* — Burns & Levinson LLP; Joseph M. Maraia (57) ABSTRACT A tissue graft attachment device includes a platform member including a first edge and a second edge connected to the first edge by a top side and a substantially curved bottom side. The platform member defines a slot extending between the first edge and the second edge, a first opening between the slot and the first edge, and a second opening between the slot and the second edge. The tissue graft attachment device includes a first filament passing through the first opening, a second filament passing through the second opening, and a graft connecting element passing through the slot to form a loop.

15 Claims, 10 Drawing Sheets (56) References Cited

U.S. PATENT DOCUMENTS

| | | |
|---|---|---|
| 7,097,654 B1 | 8/2006 | Freedland |
| 2001/0041938 A1 | 11/2001 | Hein |
| 2002/0173788 A1 | 11/2002 | Bojarski et al. |
| 2006/0064125 A1 | 3/2006 | Henderson et al. |
| 2007/0049944 A1 | 3/2007 | Stone et al. |
| 2007/0109665 A1 | 5/2007 | Wakazono |
| 2007/0233241 A1 | 10/2007 | Graf et al. |
| 2008/0046009 A1 | 2/2008 | Albertorio et al. |
| 2010/0256677 A1 | 10/2010 | Albertorio et al. |
| 2010/0324676 A1 | 12/2010 | Albertorio et al. |

FOREIGN PATENT DOCUMENTS

| | | |
|---|---|---|
| WO | 9720522 A | 6/1997 |
| WO | 2007109665 A1 | 9/2007 |

OTHER PUBLICATIONS

International Search Report and Written Opinion for PCT/US2012/057719 mailed Dec. 19, 2012.
Examination Report from related Australian Application No. 2012315897 issued May 10, 2016.

ATTACHMENT DEVICE TO ATTACH TISSUE GRAFT

CROSS REFERENCE TO RELATED APPLICATIONS

This application is a Divisional of U.S. patent application Ser. No. 13/248,598, filed Sep. 29, 2011, entitled ATTACHMENT DEVICE TO ATTACH TISSUE GRAFT, the content of which is hereby incorporated by reference in its entirety.

TECHNICAL FIELD

This document relates to tissue graft attachment.

BACKGROUND

An anterior cruciate ligament (ACL) that has ruptured and is non-repairable is generally replaced arthroscopically by a tissue graft. The tissue graft can be harvested from a portion of a patellar tendon having so called "bone blocks" at each end, and from the semitendonosis and gracilis. Alternatively, the tissue graft can be formed from synthetic materials or from a combination of synthetic and natural materials.

The replacement tissue graft is implanted by securing one end of the tissue graft in a socket formed in a passage within the femur, and passing the other end of the graft into a passage formed in the tibia.

A graft attachment device, e.g., a fixation button, can be used to secure the tissue graft at the femoral cortex, as described in U.S. Pat. No. 5,306,301 ("the '301 patent") hereby incorporated by reference in its entirety. When using a fixation button, the femoral passage generally includes a relatively larger diameter portion for receiving the graft, and a smaller diameter, passing channel near the femoral cortex for receiving a length of suture that runs from the tissue graft to the fixation button. By measuring the total length of the femoral passage and the length of the larger diameter portion of the femoral passage, the surgeon determines the appropriate length of suture material for attaching the fixation button to the tissue graft.

SUMMARY

According to one aspect, a tissue graft attachment device includes a platform member including a first edge and a second edge connected to the first edge by a top side and a substantially curved bottom side. The platform member defines a slot extending between the first edge and the second edge, a first opening between the slot and the first edge, and a second opening between the slot and the second edge. The tissue graft attachment device includes a first filament passing through the first opening, a second filament passing through the second opening, and a graft connecting element passing through the slot to form a loop.

Implementations of this aspect may include one or more of the following features.

The slot extends along a central axis. The first opening and the second opening are formed on the central axis. The first opening and the second opening each have a substantially circular cross-section. The slot extends substantially to a central location between the first edge and the second edge. The slot is defined by a first inner edge and a second inner edge connected by a first inner side positioned between a central axis and the bottom side and a second inner side positioned between the central axis and the top side. The first inner side defines a shoulder near the central location. A retaining mechanism is disposed on the second inner side. The retaining mechanism includes a leaf spring extending from the second inner side to the shoulder. The top side is substantially curved. The top side and the bottom side are defined by a respective first radius of curvature and a second radius of curvature. The first radius of curvature is different from the second radius of curvature. The graft connecting element is a third filament. The graft connecting element is a rigid band. The device further includes a first side surface connecting the first edge, the second edge, the top side, and the bottom side. The device also includes a second side surface connecting the first edge, the second edge, the top side, and the bottom side. The slot spans a distance between the first side surface and the second side surface. The first opening spans the distance between the first side surface and the second side surface. The second opening spans the distance between the first side surface and the second side surface.

According to another aspect, a method for attaching a tissue graft includes providing a tissue graft attachment device, forming a bone tunnel, manipulating the platform member using a first filament attached to the first edge to pull the platform member with the graft connecting element at a first end of the slot through the bone tunnel, and manipulating the platform member using a second filament attached to the second edge to position the platform member with the graft connecting element at a second end of the slot over the bone tunnel.

Implementations of this aspect may include one or more of the following features. The slot extends substantially to a central location between the first edge and the second edge. The platform member is positioned such that the central location is positioned substantially in a center of the bone tunnel. Manipulating the platform member using the second filament attached to the second edge includes manipulating the platform member to position the second end of the slot over substantially a center of the bone tunnel. The slot defines a shoulder. Manipulating the platform member to position the second end of the slot over substantially the center of the bone tunnel causes the graft connecting element to abut against the shoulder. The platform member includes a leaf spring extending across the slot. The platform member is manipulated to position the graft connecting element between the leaf spring and the second end of the slot. Manipulating the platform member using the first filament includes pulling the first filament to pull the platform member, first edge first, through the bone tunnel. The platform member is manipulated using the first filament to position the platform member over the bone tunnel.

According to another aspect, a method for loading a filament in a tissue graft attachment device includes providing the tissue graft attachment device, and coupling the filament to the platform member and the graft connecting element such that manipulating the filament moves the graft connecting element in the slot.

Implementations of this aspect may include one or more of the following features. The tissue graft device includes a first opening between the slot and the first edge, and a second opening between the slot and the second edge. Coupling the filament to the platform member and the graft connecting element includes passing a first end of a filament through the first opening, the second opening, the slot, and the loop formed in the graft connecting element, such that pulling either the first end or a second end of the filament pulls the graft connecting element towards the first edge. Passing the first end of the filament through the first opening, the second opening, the slot, and the loop includes passing the first end through the second opening. After passing the first end through the second opening, the first end is passed through the first opening. After passing the first end through the first opening, the first end is passed through the slot. After passing the first end through the slot, the first end is passed through the first opening. After passing the first end through the first opening, passing the first end through the slot includes passing the first end through the loop.

According to another aspect, a tissue graft attachment device includes a platform member including a first edge and a second edge connected to the first edge by a top side and a bottom side. The platform member defines a slot extending between the first edge and the second edge. A graft connecting element passes through the slot to form a loop. The device includes a filament coupled to the platform member and the graft connecting element such that manipulating the filament moves the graft connecting element in the slot.

Implementations of this aspect may include one or more of the following features. The device includes a first opening between the slot and the first edge, and a second opening between the slot and the second edge. A first end of the filament is passed through the first opening, the second opening, the slot, and the loop formed in the graft connecting element such that pulling either the first end or a second end of the filament pulls the graft connecting element towards the first edge. The first end of the filament, which is passed through the first opening, the second opening, the slot, and the loop, is passed through the second opening, is passed through the first opening after being passed through the second opening, is passed through the slot after being passed through the first opening, and is passed through the first opening after being passed through the slot. The first end passed through the slot after being passed through the first opening further includes the first end passed through the loop.

The details of one or more implementations are set forth in the accompanying drawings and the description below. Other features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

This document describes an example of an attachment device to attach tissue grafts. The attachment device can be implemented in an endoscopic technique for graft attachment in reconstruction surgery. For example, in an ACL reconstruction surgery, a medial portal incision or a transtibial approach is made and a tunnel is created either from inside the joint space or from the outside. A tissue graft is attached to a platform member included in an attachment device, for example, using a graft connecting element such as a closed looped suture or a closed loop of flexible material. The platform member is then passed through the tunnel. After the platform member, in its entirety, exits the tunnel, the attachment device is positioned on the cortex such that the tissue graft passes into the tunnel. To position the attachment device on the cortex, in some situations, the platform member may be turned (for example, flipped) from one orientation (for example, a substantially vertical orientation) in which the platform member is passed through the tunnel to another orientation (for example, a substantially horizontal orientation) in which the platform member is positioned on the cortex. As described below, the design of the platform member can cause the platform member to turn for positioning on the cortex. Alternatively or in addition, the platform member can be turned, for example, by pulling on a removable filament (for example, a suture, a tape, and the like) or pulling on the graft, and positioned on the cortex.

Depending upon a location at which the graft connecting element (for example, a looped suture) is attached to the platform member, a length of the graft connecting element that passes out of the tunnel when the platform member is pulled through the tunnel in one direction may return into the tunnel in the opposite direction when the platform member turns or is turned and positioned on the cortex. This length of the graft connecting element, in turn, may affect an amount of tissue graft that passes back out of the tunnel through the opposite opening, thereby reducing the amount of tissue graft that remains in the tunnel. In various implementations described in this document, this length of the looped suture is minimized or reduced, which may result in an amount of the tissue graft in the tunnel being maximized because shorter graft connecting elements can be used relative to designs that do not minimize this length. Consequently, losses in the amount of the tissue graft remaining in the tunnel may also be reduced. In addition, the platform member can be configured to allow positioning and retaining the tissue graft in substantially a center of the cortex in various implementations of the attachment device described in this document.

Figure 1A:
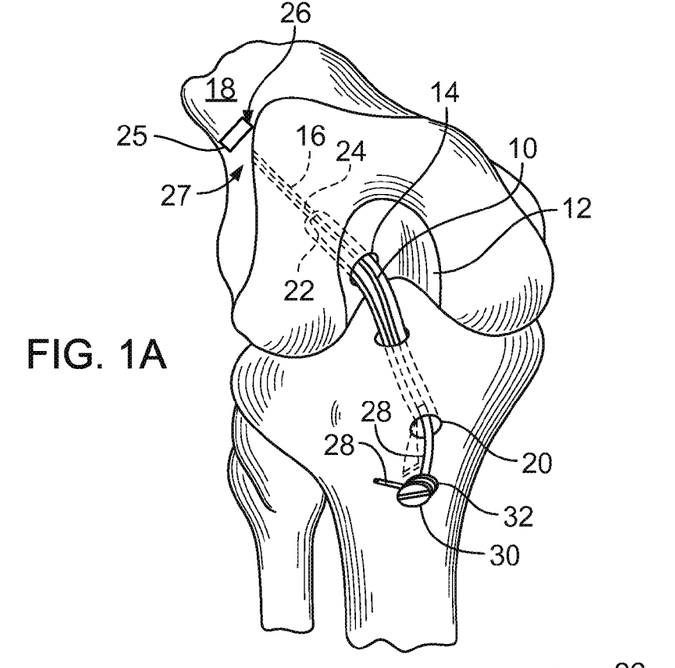
FIGS. 1A and 1B are illustrations of a tissue graft secured within the knee by a graft attachment device.
Figure 1B:
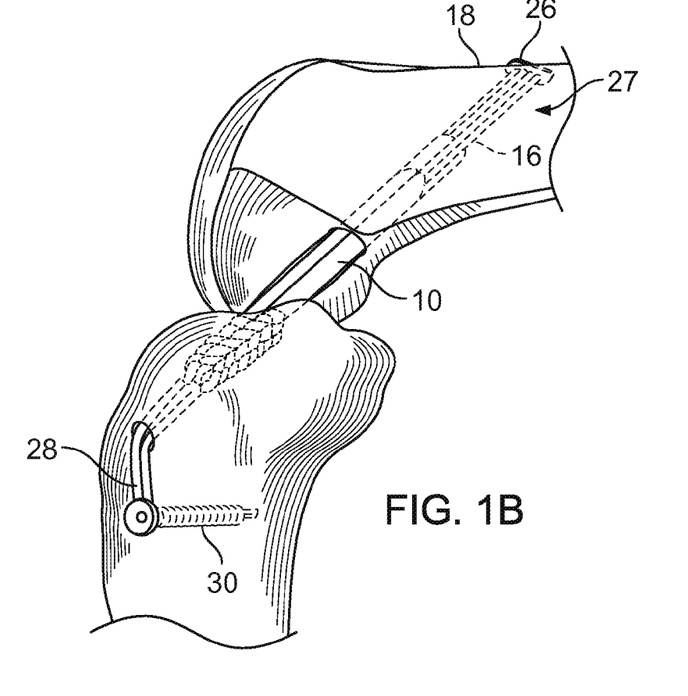

Referring to FIGS. 1A and 1B, a knee joint has a tissue graft 10 (e.g., a patellar tendon graft (FIG. 1A) or a semi-tendonosis and gracilis graft (FIG. 1B)) implanted in an anterior cruciate ligament (ACL) repair and reconstruction procedure. A femoral channel 14 for receiving one end of tissue graft 10 is drilled from the intercondylar notch 12 a predetermined distance within the femur 27 with a passing channel 16 of reduced diameter drilled further through the femur 27 from femoral channel 14 to a region of femoral cortex 18. A tibial channel 20 for receiving the other end of tissue graft 10 is drilled from an anterior region of the tibia.

In the case of patellar tendon graft, one end of tissue graft 10 includes a bone block 22 which is shaped and sized in close conformity with femoral channel 14 to ensure optimal healing. A graft attachment device 25 includes a graft connecting element 24 and a platform member 26. A length of the graft connecting element 24 (for example, a suture, multiple knotted or looped sutures, and the like) has one end attached to bone block 22 and the other end secured at femoral cortex region 18 with the platform member 26. The graft connecting element 24 may be, for example, a woven or braided suture, for example, #5 Ultrabraid suture, attached to the platform member 26 in a loop configuration. In some implementations described below, one end of the tissue graft 10 is attached to the platform member 26, which is then pulled into the femoral channel 14. The platform member 26 may be configured to maximize an amount of the tissue graft 10 in the femoral channel 14. The other end of tissue graft 10 includes a second length of a graft connecting element 28 which is attached to the tibia, for example, with a fixation screw 30. A washer 32 either attached to or positioned under the head of fixation screw 30 helps in holding the graft connecting element in place when screw 30 is tightened.

Figure 2:
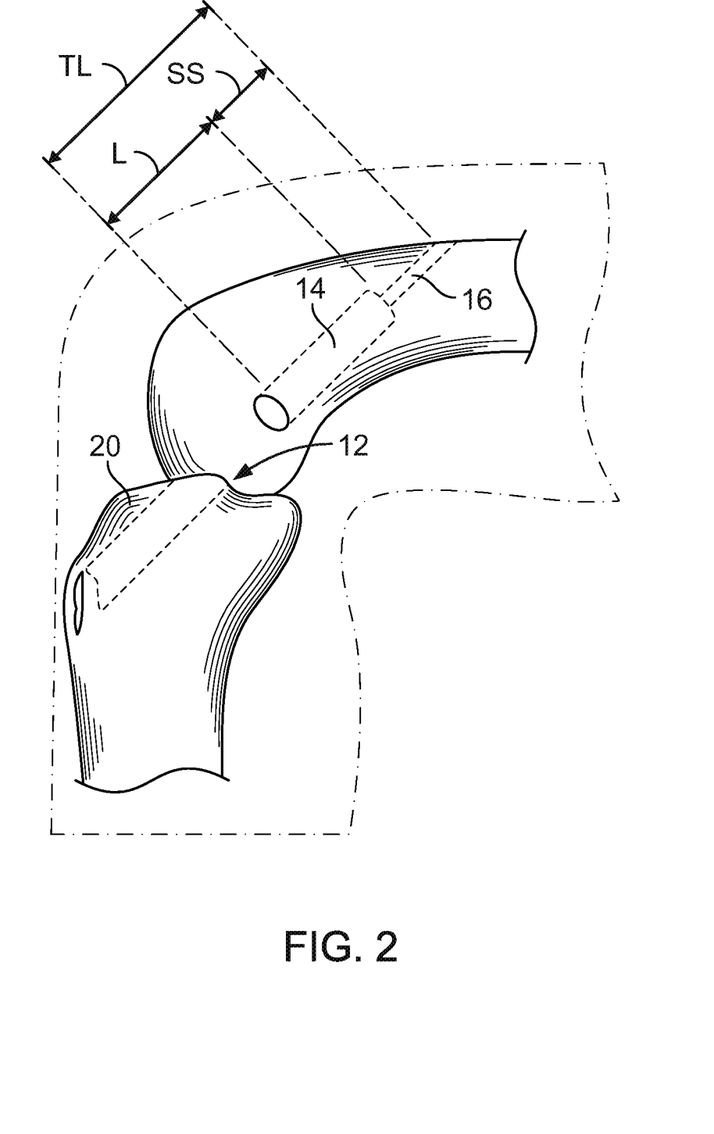
FIG. 2 is another view of the knee joint of FIGS. 1A and 1B.

Referring to FIG. 2, length (L) of femoral channel 14 is selected by the surgeon in accordance with the length of bone block 22 and the desired insertion distance of tissue graft 10 within the femur 27. The span of the graft connecting element 24, designated as SS, is approximately that of passing channel 16 so that the sum of the desired insertion length (L) and span of the graft connecting element (SS) is the measured total length (TL) from the opening of femoral channel 14 to the opening at femoral cortex 18. Each of these dimensions is measured prior to implanting the tissue graft so that during the implantation procedure, the surgeon, under arthroscopic observation, can be assured that tissue graft 10 has been properly positioned within femoral channel 14.

Figure 3A:
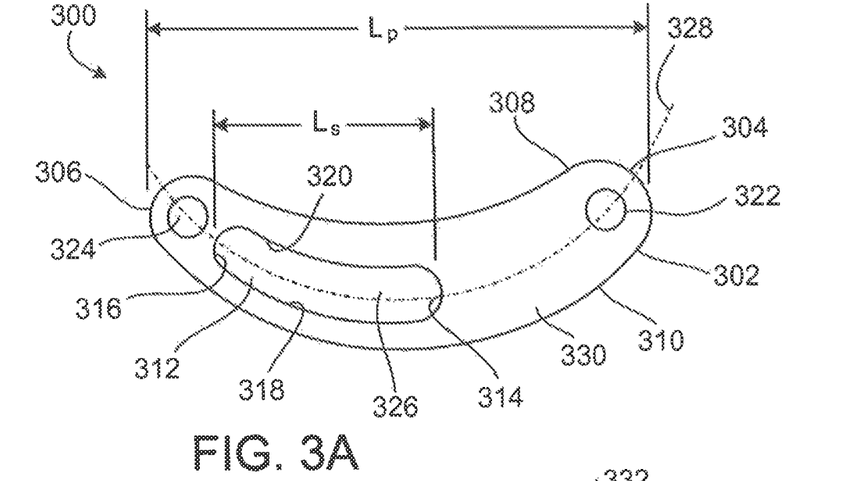
FIGS. 3A and 3B are a side view and a plan view, respectively, of a platform member.
Figure 3B:
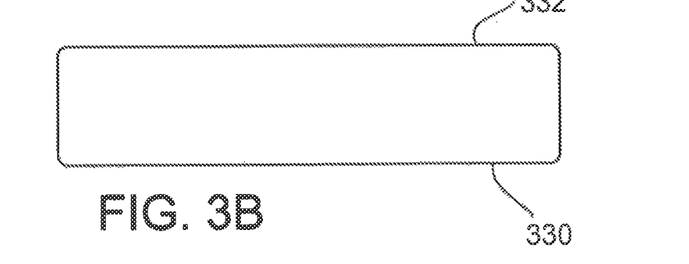

FIGS. 3A and 3B are a side view and a plan view, respectively, of a platform member 302 that is included in an attachment device 300 (FIG. 3C), for example, the platform member 26. The attachment device 300 includes a platform member 302 that defines a slot 312. The attachment device 300 additionally includes a graft connecting element 340 (for example, a looped suture, multiple looped sutures, multiple knotted sutures, a rigid or stretchable band, and the like), which is passed through the slot 312 to form a loop, and to which a tissue graft is attached. The attachment device 300 is passed through a bone tunnel, for example, the femoral channel 14. As described below, the platform member 302 is configured to maximize the amount of tissue graft that resides in the bone tunnel after the attachment device 300 is deployed, for example, by minimizing a length of the graft connecting element 340 that returns into a bone tunnel after the platform member 302 is pulled through the bone tunnel, and turned and positioned on the cortex of the bone tunnel. Such minimizing allows a surgeon to maximize the amount of tissue graft that is in the tunnel after the attachment device 300 has been deployed. In addition, the platform member 302 is configured to allow the graft connecting element 340 to be positioned and retained at substantially at a center of the bone tunnel.

The platform member 302 has a first edge 304 and a second edge 306 connected to the first edge 304 by a top side 308 and bottom side 310, and defines a length ($L_p$, for example, 8 mm to 25 mm). The first edge 304 and the second edge 306 can each be substantially curved or substantially flat to define a width, for example, 3 mm to 10 mm. The bottom surface 310 is substantially curved. In some implementations, the top side 308 is also substantially curved, while in others, the top side 308 is substantially flat. For example, the top side 308 and the bottom side 310 have respective radii of curvature, which are different from each other. As described below, the radius of curvature of the bottom side 310 is such that the bottom side 310 is in substantially continuous contact with an outlet of the bone tunnel when the platform member 302 is manipulated (for example, turned) to position the platform member 302 over the outlet of the bone tunnel.

In some implementations, the first edge 304 and the second edge 306 can each be a surface (FIG. 3C), while in others, the first edge 304 and the second edge 306 can each be an edge where the top surface 308 meets the bottom surface 310. The radii of curvature of the top side 308 and the bottom side 310 can be the same as or different from each other. For example, both surfaces (the first surface 308 and the second surface 310) can be convex.

Figure 3C:
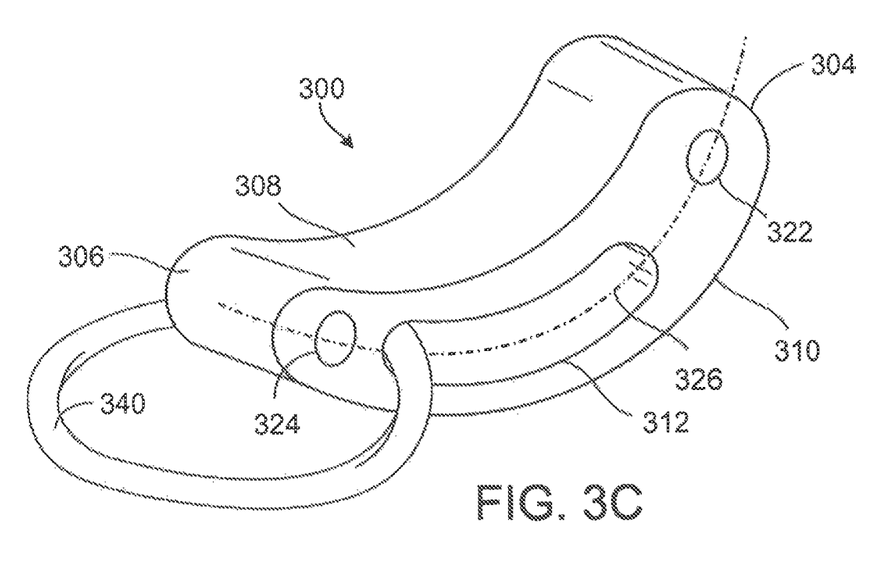
FIG. 3C is a perspective view of an attachment device including the platform member of FIGS. 3A and 3B, and an graft connecting element.

The platform member 302 defines a slot 312 (for example, of length $L_s$) extending between the first edge 304 and the second edge 306. For example, the slot 312 extends along a central axis 328 of the platform member 302. A width of the slot 312 is sufficient to pass the graft connecting element 340 through the slot 312 (FIG. 3C). The slot 312 is defined by a first inner edge inner edge 314 and an second inner edge 316, which can each be either substantially flat or substantially curved. The first inner edge inner edge 314 is closer to the first edge 304 than the second inner edge 316. Further, the second inner edge 316 is formed as close to the second edge 306 as possible, taking into account, for example, machining and manufacturing tolerances, as well as structural integrity. During use, this may minimize or reduce the length of graft connecting element or other attachment member used to hold the tissue graft.

The first inner edge inner edge 314 and the second inner edge 316 are connected by a first inner side 318 positioned between the central axis 328 and the bottom side 310, and a second inner side 320 positioned between the central axis 328 and the top side 308. In some implementations, both inner sides (the first inner side 318 and the second inner side 320) can both be positioned between the central axis 328 and the bottom side 310. Also, the first inner side 318 and the second inner side 320 may or may not be substantially parallel to the bottom side 310 and the top side 308, respectively. The first inner side 318 is formed as close to the bottom side 310 as possible, taking into account, for example, machining and manufacturing tolerances, as well as structural integrity. In addition, the slot 312 can be formed along a slot axis 326, which may or may not be substantially parallel or substantially collinear (or both) with the central axis 328.

The platform member 302 includes a first side surface 330 and a second side surface 332 (FIG. 3B), each connecting the first edge 304, the second edge 306, the top surface 308, and the bottom surface 310. The slot 312 is defined to span a distance between the first side surface 330 and the second side surface 332 (FIG. 3C). The slot 312 extends substantially to a central location between the first edge 304 and the second edge 306 in the first side surface 330. For example, the first inner edge 316 can be defined substantially at a center of the platform member 302. In this manner, the first inner edge 316 forms a boundary against which the graft connecting element 340 abuts when the platform member 302 is manipulated and positioned over the bone tunnel.

The platform member 302 additionally defines a first opening 322 between the first edge 304 and the second edge 306. The first opening 322 is formed between the first inner edge 314 and the first edge 304, for example, as close to the first edge 304 as possible subject to machining and manufacturing tolerances as well as structural integrity. The platform member 302 also defines a second opening 324 between the slot 312 and the second edge 306. The second opening 324 is formed as close to the second edge 306 as possible away from a surface of the platform member 302 bounded by the second inner edge 316, at least a portion of the second edge 306, and at least a portion of the bottom side 308. For example, due to the curvature of the bottom side 310, the second opening 324 and the second inner edge 324 can both be formed to be as close to the second edge 306 as possible such that the second opening 324 and the second inner edge 324 lie on the same horizontal line when the platform member 302 is in a substantially vertical orientation.

The first opening 322 and the second opening 324 are formed on the central axis 328 of the platform member 302. In some implementations, either the first opening 322 or the second opening 324 (or both) can be formed away from the central axis 328. Each of the first opening 322 and the second opening 324 is formed in the first side surface 330 and spans the distance between the first side surface 330 and the second side surface 332. In some implementations, either the first opening 322 or the second opening 324 (or both) can be formed in the top surface 308 and span a distance between the top surface 308 and the bottom surface 310. Each of the first opening 322 and the second opening 324 has a substantially circular cross-section. In some implementations, the openings (the first opening 322 and the second opening 324) can have any cross-section (for example, square, rectangular).

Figure 4A:
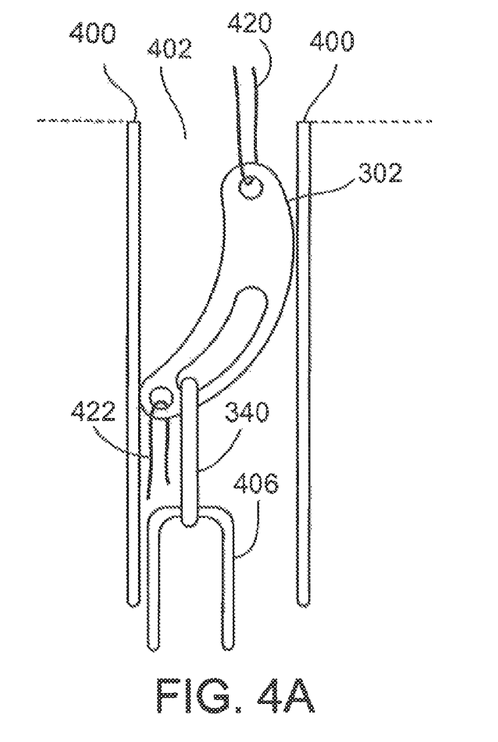
FIG. 4A is a side view of the attachment device being pulled through a bone tunnel.
Figure 4B:
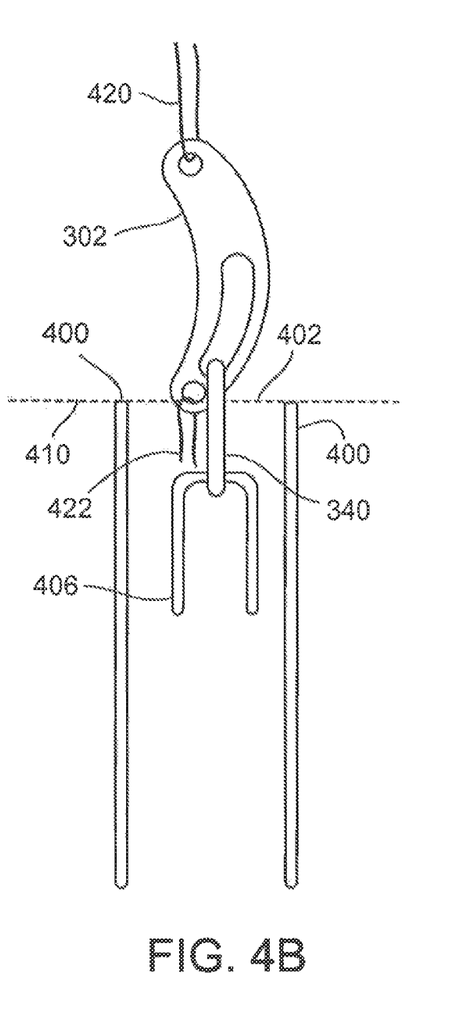
FIG. 4B is a side view of the attachment device of 4A being pulled out of the bone tunnel.
Figure 4C:
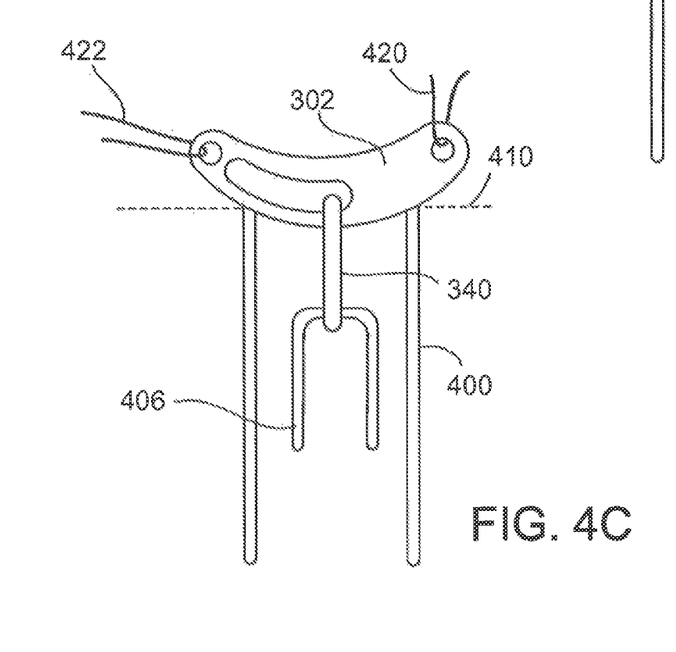
FIG. 4C is a side view of the attachment device of 4A being positioned over the bone tunnel.

In some implementations, the attachment device 300 is pre-loaded to include a first removable filament 420 and a second removable filament 422 (FIGS. 4A-4C). Specifically, the first removable filament 420 is passed through the first opening 322 and the second removable filament 422 is passed through the second opening 324. The dimensions of the openings (the first opening 322 and the second opening 324) are sufficient to receive the respective filaments (a first removable filament 420 and a second removable filament 422) through the openings (the first opening 322 and the second opening 324).

In alternative implementations, the attachment device 300 can have only one opening (either the first opening 322 or the second opening 324) or no opening. For example, in implementations in which the attachment device 300 includes only the first opening 322, the first filament 420 can be passed through the first opening 322 to attach the first filament 420 to the platform member 302 and the second filament 422 can be passed through the slot 312 between the second inner edge 316 and the graft connecting element 340. In another example in which the attachment device 300 includes only the second opening 324, the first filament 420 can be passed through the slot 312 between the graft connecting element 340 and the first inner edge 314, and the second filament 422 can be passed through the second opening 324. In yet another example in which the attachment device 300 includes no opening, the first filament 420 and the second filament 422 can be passed through the slot between the first inner edge 314 and the graft connecting element 340, and between the graft connecting element 340 and the second inner edge 316, respectively.

FIGS. 4A, 4B, and 4C are side views of the attachment device 300 being pulled through a bone tunnel, being pulled out of the bone tunnel, and being positioned over the bone tunnel, respectively. The bone tunnel 400 can be, for example, 3.5 mm in diameter and have a substantially vertical or angular orientation. A tissue graft 406 is attached to the graft connecting element 340, and particularly to the loop formed in the graft connecting element 340. The platform member 302 is then manipulated using the first filament 420 to pull the platform member 302, to which the graft connecting element 340 is attached, through the bone tunnel 400. For example, the first filament 420 is pulled through the bone tunnel 400 causing the platform member 302, which is attached to the first filament 420, to be pulled through the bone tunnel 400. When the platform member 302 is pulled into the bone tunnel 400, the graft connecting element 340 is also pulled into the bone tunnel 400. Because the tissue graft 406 is attached to the graft connecting element 340 and because the second filament 422 is attached to the platform member 302, the tissue graft 406 and the second filament 422 are also pulled into the bone tunnel 400. At this stage, the central axis 328 of the platform member 302 can be substantially parallel to an axis of the bone tunnel 400.

As the platform member 302 is pulled out of the bone tunnel 400 (FIG. 4B), the graft connecting element 340 slides towards and rests against the second inner edge 316 of the slot 312. As described above, the second inner edge 316 is formed as near the second edge 306 as possible. Because the graft connecting element 340 moves to the second inner edge 316, the length of the graft connecting element 340 needed is shorter than if the graft connecting element 340 was connected elsewhere on the platform member 302 (for example, the center). This is the result of the graft connecting element 340 needing to be longer at other attachment points to allow the platform member 302 to fully exit the bone tunnel 400. A shorter loop 340 can result in minimizing the distance by which the platform member 302 needs to be turned to position the platform member 302 on the outlet 402 of the bone tunnel 400, and also in greater engagement of the tissue graft 406 with the bone when compared to a longer loop.

When the platform member 302 exits the outlet 402 of the bone tunnel 400, the second inner edge 316 first exits the outlet 402 followed by the second edge 306. In this position, the platform member 302 rotates about the central axis 328 from a position in which the central axis 328 of the platform member 302 is substantially parallel to the axis of the bone tunnel 400 to a position in which the central axis 328 is substantially perpendicular to the axis of the bone tunnel 400.

In some implementations, the platform member 302 rotates due to the curvature of the bottom side 310. Alternatively, or in addition, the platform member 302 is manipulated using the second filament 422 to position the platform member 302 over the outlet 402 of the bone tunnel 400. As shown in FIG. 4C, the second filament 422 is pulled, for example, in a direction transverse to a longitudinal axis 410 of the bone tunnel 400, to position the platform member 302 over the outlet 402. As the second filament 422 is pulled, the bottom side 310 of the platform member 302 is in substantially continuous contact with the outlet 402 due to the curvature of the bottom side 310. The substantially continuous contact can result in a decrease in a length of the graft connecting element 340, which exits and then returns into the bone tunnel 400, when the platform member 302 is turned. Consequently, relative to platform members that have a substantially flat bottom side, the platform member 302 can minimize a length of the graft connecting element 340 and result in greater engagement of the tissue graft 406 with the bone.

As described above, the slot 312 extends substantially to a central location between the first edge 304 and the second edge 306. In other words, the first inner edge 314 is defined at the central location. When the platform member 302 is turned and positioned on the outlet 402 of the bone tunnel 400, the central location, and consequently the first inner edge 314, is positioned substantially in a center of the bone tunnel 400. In situations in which the bone tunnel 400 has a substantially vertical orientation, the graft connecting element 340 slides along the first inner side 318 that defines the slot 312 toward the first inner edge 314 due to the curvature of the first inner side 318. The graft connecting element 340 ceases to slide upon abutting the first inner edge 314. Because the first inner edge 314 is positioned at substantially the center of the bone tunnel 400, the graft connecting element 340, and consequently the tissue graft 406, is also positioned at substantially the center of the bone tunnel 400. In situations in which the bone tunnel 400 has an angular or horizontal orientation, the graft connecting element 340 slides toward and abuts the first inner edge 314 due to gravity or the curvature of the first inner side 318 or both.

Figure 5A:
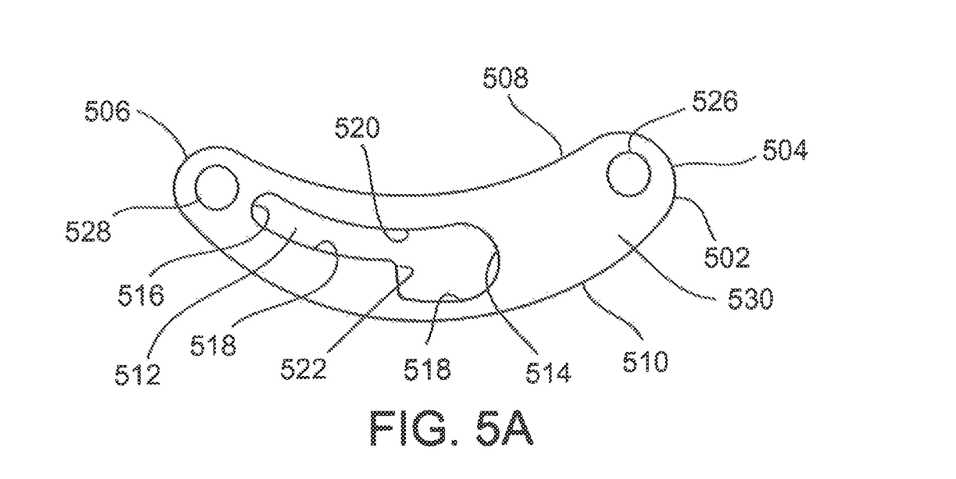
FIGS. 5A and 5B are a side view and a plan view, respectively of a platform member including a slot that defines a shoulder.
Figure 5B:
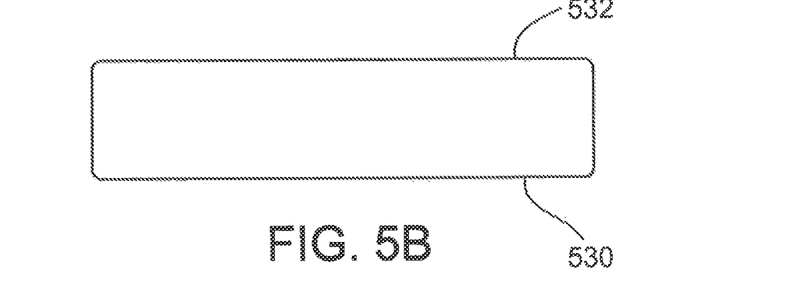

FIGS. 5A and 5B are a side view and a plan view, respectively of an alternative platform member 502 including a slot 512 that defines a shoulder 522. Similarly to the platform member 302, the platform member 502 includes a first edge 504 and a second edge 506 connected to the first edge 504 by a top side 508 and a substantially curved bottom side 510. The platform member 502 defines a slot 512 extending between the first edge 504 and the second edge 506. The slot 512 is formed in a first side surface 530 and spans a distance from the first side surface 530 to the second side surface 532. The platform member 502 further defines a first opening 526 between the slot 512 and the first edge 504, and a second opening 528 between the slot 512 and the second edge 506.

The slot 512 is defined by an first inner edge 514 and an second inner edge 516 connected by a first inner side 518 positioned between a central axis of the platform member 502 and the bottom side 510, and a second inner side 520 positioned between the central axis and the top side 508. The slot 512 extends substantially to a central location of the platform member 502 between the first edge 504 and the second edge 506. The first inner side 518 defines a shoulder 522 near the central location. For example, a width of the slot 512 (i.e., a distance between the first inner side 518 and the second inner side 520) from the second inner edge 516 to the shoulder 522 can be less than a width of the slot 512 from the shoulder 522 to the first inner edge 514.

Similarly to the platform member 302, the platform member 502 is manipulated to pull the platform member 502 through a bone tunnel (not shown), and to turn and position the platform member 502 over an outlet of the bone tunnel. The first inner edge 514 can be positioned over substantially a center of the bone tunnel. In such situations, an graft connecting element (not shown), which is passed through the slot 512 to form a loop and to which a tissue graft is attached, slides from the second inner edge 516 toward the first inner edge 514. The graft connecting element drops into the region of the slot between the shoulder 522 and the first inner edge 514. The graft connecting element is abutted by the first inner edge 514 on one side and the shoulder 522 on the other side. In this manner, a position of the graft connecting element, and consequently the tissue graft attached to the graft connecting element, over substantially the center of the bone tunnel is maintained. An example of an attachment device including the platform member 502 is shown in FIG. 5D. The attachment device includes the graft connecting element 340 to which a tissue graft 406 is attached.

Figure 5C:
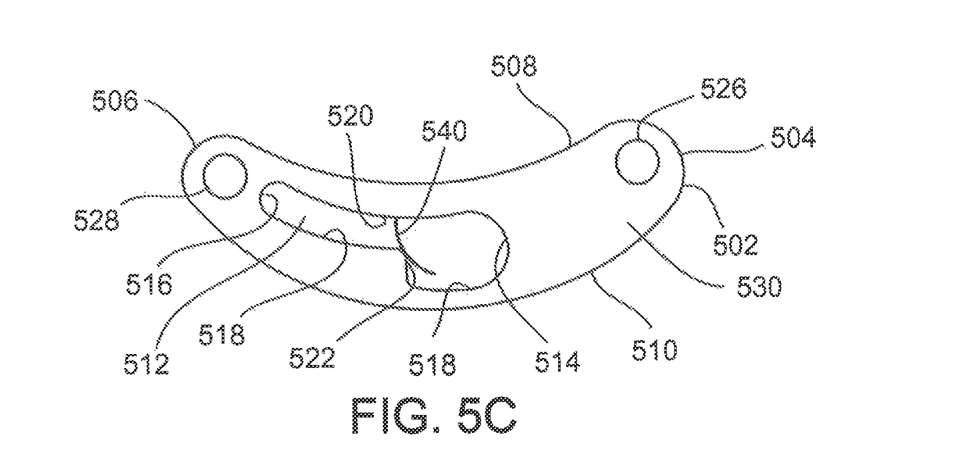
FIG. 5C is a side view of an alternate version of the platform member of FIG. 5A that includes a retaining mechanism.
Figure 5D:
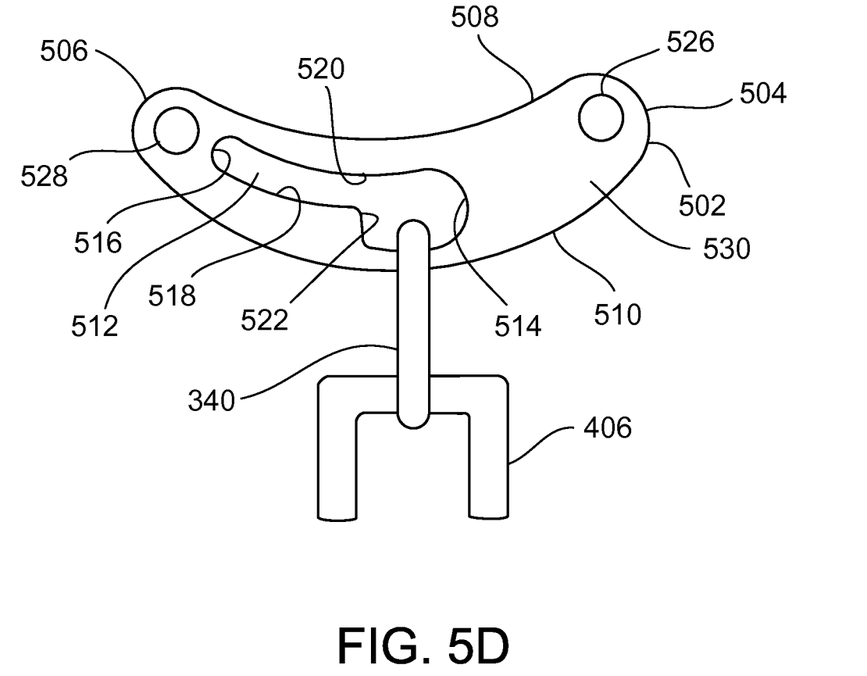
FIG. 5D is a side view of an attachment device including the platform member of FIGS. 5A and 5B.

FIG. 5C is a side view of an alternative version of the platform member 502 of FIG. 5A that includes a retaining mechanism 540. For example, the retaining mechanism 540 includes a leaf spring hinged to a position on the second inner side 520 and extending over the shoulder 522. Alternatively, the retaining mechanism 540 can be hinged to a position on the first inner side 518 near the shoulder 522 and extend toward the second inner side 520. The retaining mechanism 540 swings about the hinged position toward the first inner edge 514. The shoulder 522 interferes with the retaining mechanism 540 when the retaining mechanism 540 swings about the hinged position toward the second inner edge 516. In some situations, the graft connecting element (not shown) is pre-loaded in the slot 512 between the second inner edge 516 and the retaining mechanism 540. When the platform member 502 is pulled through the bone tunnel, and turned and positioned over the outlet of the bone tunnel, the graft connecting element slides toward the first inner edge 514 as described previously. Because the retaining mechanism 540 can swing about the hinged position toward the first inner edge 514, the retaining mechanism 540 permits the graft connecting element to cross the retaining mechanism 540 and slide toward the first inner edge 514. However, the retaining mechanism 540 prevents the graft connecting element from crossing the retaining mechanism and sliding back toward the second inner edge 516 due the interference between the retaining mechanism 540 and the shoulder 522. In alternative implementations, the retaining mechanism 540 can be formed on either the first inner side 518 or the second inner side 520 (or both) as a wave-shaped rising surface that permits the graft connecting element to pass in one direction (for example, towards the shoulder 522) but prevents the graft connecting element from passing in the opposite direction.

The retaining mechanism can also be disposed in implementations of the platform member that do not define the shoulder. In such implementations, a retaining mechanism can be disposed in the slot such that the first inner side of the slot that is nearer the bottom side of the platform member than the second inner side of the slot interferes with the retaining mechanism. When the graft connecting element slides from the second inner edge toward the first inner edge, the retaining mechanism can swing about a hinged position (on the second inner side) toward the first inner edge to permit the graft connecting element to cross the retaining mechanism and slide toward the first inner edge. Because the retaining mechanism interferes with the first inner side of the slot, the retaining mechanism can prevent the graft connecting element from sliding back toward the second inner edge.

Figure 6A:
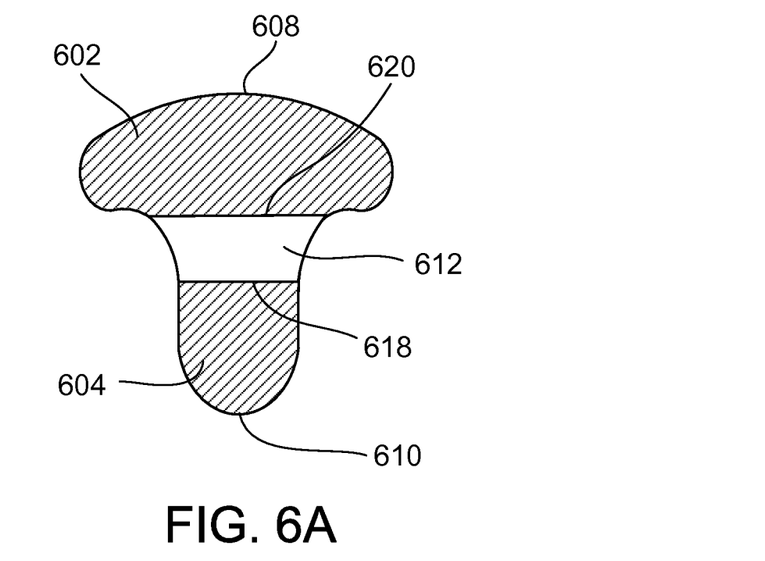
FIG. 6A is a cross-sectional view of another platform member.
Figure 6B:
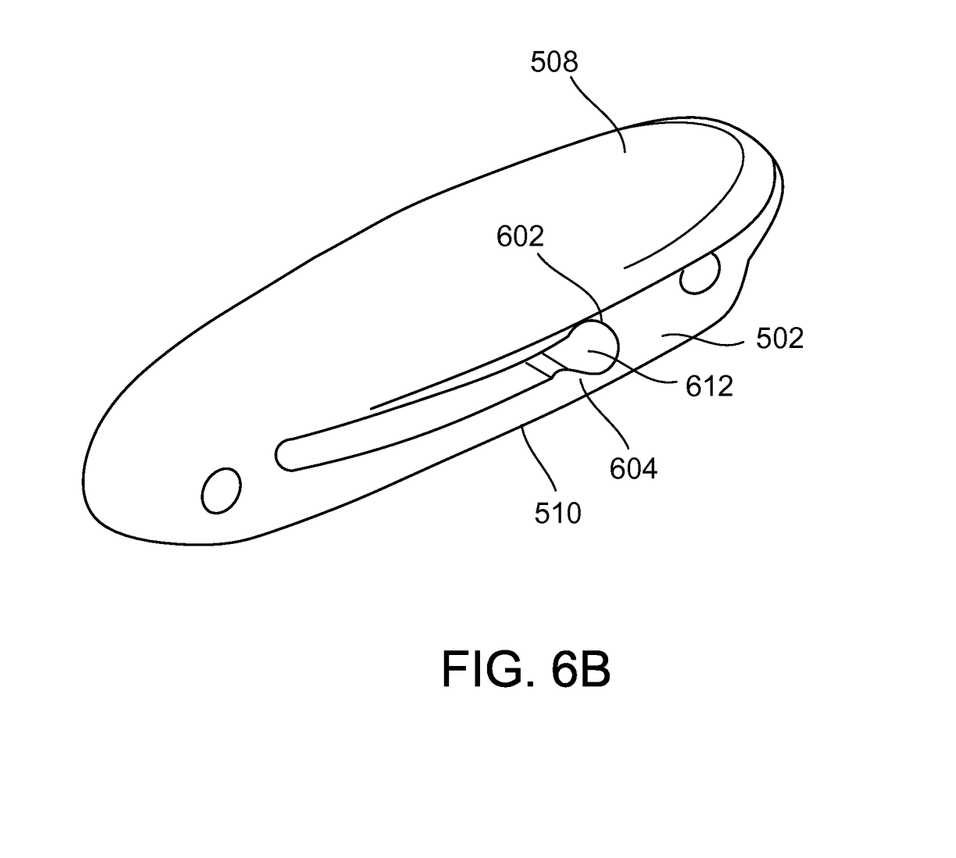
FIG. 6B is a perspective view of the platform member of FIG. 6A.

FIGS. 6A and 6B are a cross-sectional view of another platform member 600 and a perspective view of the platform member 600, respectively. A width of the platform member 600 in a first region 602 between a top surface 608 and a slot 612 (specifically, a second inner side 620) can be greater than a width of the platform member 600 in a second region 604 between the slot 612 (specifically, a first inner side 618) and a bottom surface 610.

Figure 6C:
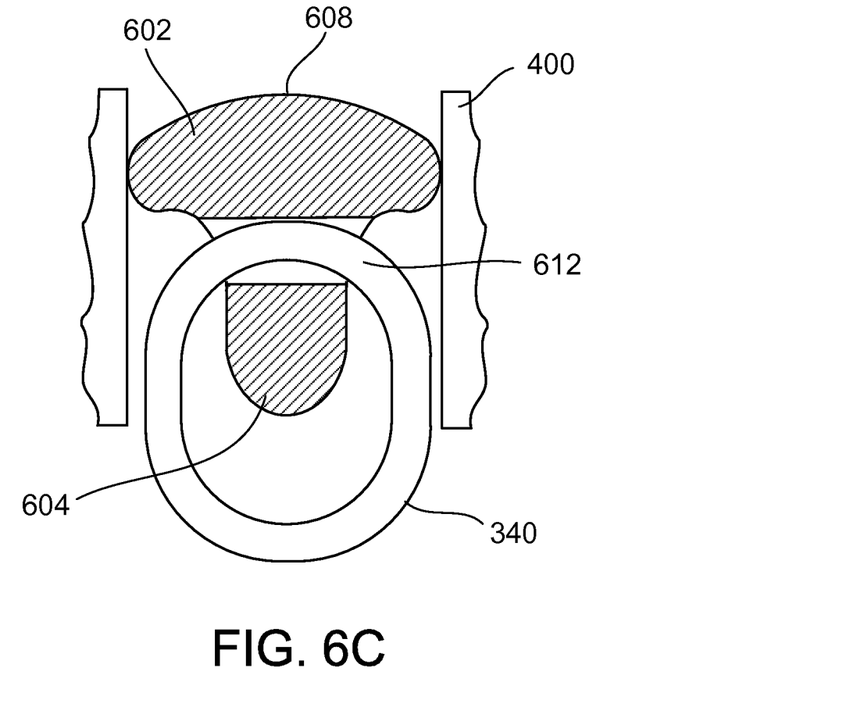
FIG. 6C is a cross-sectional view of the platform member of FIG. 6A including an graft connecting element.

FIG. 6C is a cross-sectional view of the platform member 600 including the graft connecting element 340. As shown, the width of the second region 604 is such that when an graft connecting element, for example, the graft connecting element 340, is looped through the slot 612, then a combined width of the graft connecting element and the second region 604 is less than or equal to the width of the first region 602, and the width of both regions (the first region 602 and the second region 604) is less than that of the bone tunnel 400.

Figure 7A:
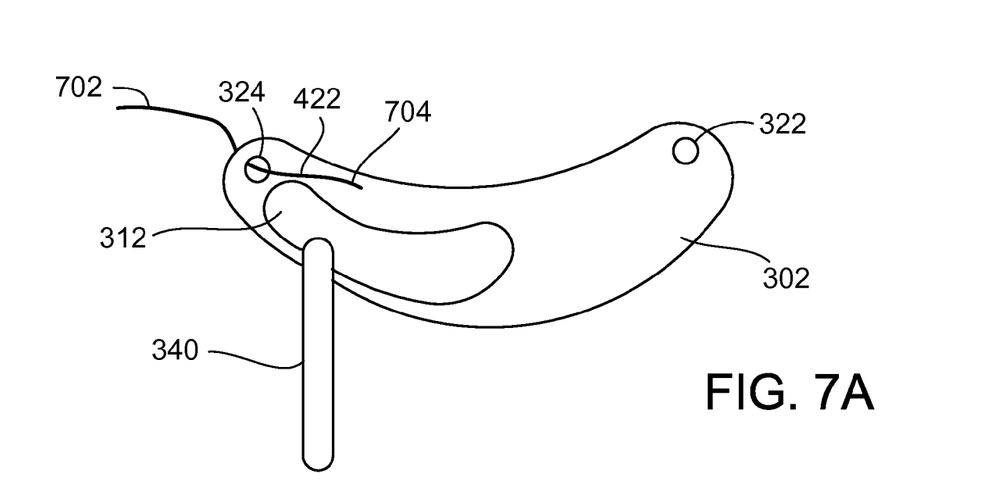
FIG. 7A-7D are side views of a platform member through which a filament is passed.
Figure 7B:
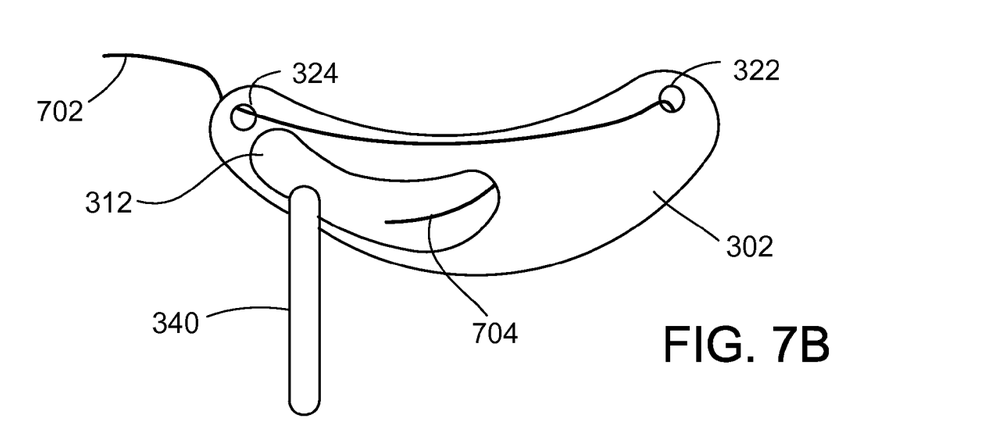
Figure 7C:
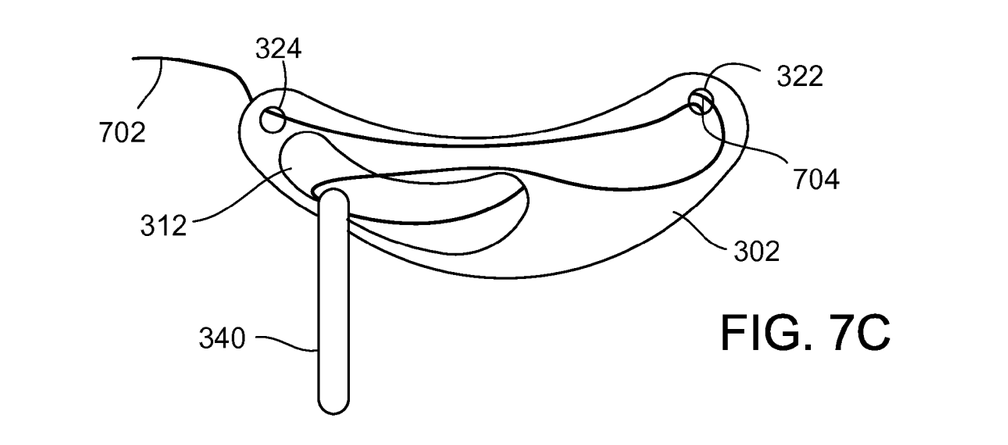
Figure 7D:
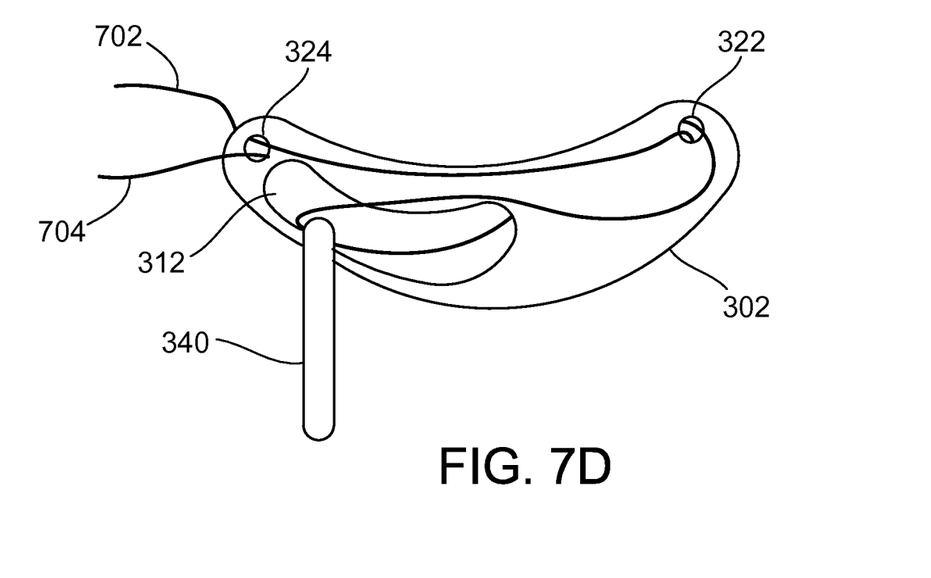

Referring to FIGS. 7A-7C, the platform member 302 (or the platform member 502) can be pre-loaded to include the first removable filament 420 and the second removable filament 422. In some implementations, the first filament 420 can be loaded into the platform member 302 such that pulling on either a first end 702 or a second end 704 of the first filament 420 pulls the graft connecting element 340 towards the first edge of the platform member 302. The second end 704 of the first filament 420 is passed through the second opening 324 of the platform member 302 (FIG. 7A). After passing the first end 704 through the second opening 324, the second end 704 is passed through the first end 322 (FIG. 7B) along a side of the platform member 302. After passing the first end 704 through the first opening 322 along a side of the platform member 302, the second end 704 is passed through the slot 312, for example, along the other side of the platform member 302 (FIG. 7C). Specifically, the second end 704 is passed through the loop formed in the graft connecting element 340. After passing the second 704 through the slot 312 (and particularly through the loop formed in the graft connecting element 340), the second end 704 is passed through the first opening 322 (FIG. 7D). When one end (either the first end 702 or the second end 704) is pulled, with the other end being held in place, then a motion of the first filament 420 through the first opening 322, the second opening 324, and the loop in the graft connecting element 340 causes the graft connecting element 340 to move toward the first edge. In this manner, after the platform member 302 is positioned over the bone tunnel 400, the graft connecting element 340 can be positioned near the first inner edge 314 of the slot 312, for example, if turning and positioning the platform member 302 over the bone tunnel 400 alone does not cause the graft connecting element 340 to slide toward the first inner edge 314.

While this specification contains many specific implementation details, these should not be construed as limitations on the scope of any implementations or of what may be claimed, but rather as descriptions of features specific to particular implementations of particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

What is claimed is:

1. A tissue graft attachment device comprising:
   a platform member comprising:
   a first edge and a second edge connected to the first edge by a top side and a substantially curved bottom side;
   a first side surface and a second side surface, each of the first side surface and the second side surface connecting the first edge, the second edge, the top surface and the bottom surface;
   a slot formed through the platform member from the first side surface to the second side surface, the slot extending between a location closer to the first edge and a substantially central location between the first edge and the second edge;
   a first opening extending through the platform member from the first side surface to the second side surface, the first opening at a location between the slot and the first edge; and
   a second opening extending through the platform member from the first side surface to the second side surface, the second opening at a location between the slot and closer to the second edge;
   wherein a portion of the first and second side surfaces extending from the substantially central location to the second opening, and from the top side to the bottom side, defines a solid surface.

2. The device of claim 1, wherein the slot extends along a central axis, and the first opening and the second opening are formed on the central axis.

3. The device of claim 1, wherein the first opening and the second opening each have a substantially circular cross-section.

4. The device of claim 1, wherein the slot is defined by a first inner edge and a second inner edge connected by a first inner side positioned between a central axis and the bottom side of the platform member and a second inner side positioned between the central axis and the top side of the platform member, and wherein the first inner side defines a shoulder near the central location.

5. The device of claim 1, wherein the top side of the platform member is substantially curved.

6. The device of claim 5, wherein the top side of the platform member and the bottom side of the platform member are defined by a respective first radius of curvature and a second radius of curvature, wherein the first radius of curvature is different from the second radius of curvature.

7. The device of claim 1 wherein the platform member defines a curved central axis, the curved slot defines a curved slot axis, and curved slot axis coincides with the curved central axis.

8. The device of claim 1, wherein the first opening and the second opening each have a cross-section that is one of square and rectangular.

9. The device of claim 1, further comprising a first filament passing through the first opening.

10. The device of claim 1, further comprising a second filament passing through the second opening.

11. The device of claim 1, further comprising a graft connecting element passing through the slot to form a loop.

12. The device of claim 11, wherein the graft connecting element is a third filament.

13. The device of claim 11, wherein the graft connecting element is a rigid band.

14. A tissue graft attachment device comprising:
   a platform member including a first edge and a second edge connected to the first edge by a top side and a bottom side, the platform member defining a slot extending between the first edge and the second edge;
   a graft connecting element passing through the slot to form a loop; and a filament coupled to the platform member and the graft connecting element such that manipulating the filament moves the graft connecting element in the slot;

wherein a first end of the filament passing through the slot after being passed through a first opening between the slot and the first edge comprises the first end passing through the loop formed by the graft connecting element.

15. The device of claim 14, wherein the first end of the filament passed through the first opening, the slot, and the loop further comprises:

the first end passed through a second opening between the slot and the second edge;

the first end passed through the first opening after being passed through the second opening;

the first end passed through the slot after being passed through the first opening; and the first end passed through the first opening after being passed through the slot.

\* \* \* \* \*